(12) United States Patent
Weber et al.

(10) Patent No.: US 10,816,890 B2
(45) Date of Patent: Oct. 27, 2020

(54) X-RAY PHOSPHOR PLATE SYSTEM

(71) Applicant: Dürr Dental SE, Bietigheim-Bissingen (DE)

(72) Inventors: Michael Weber, Burgstetten (DE); Bernd Philipps, Untergruppenbach (DE)

(73) Assignee: DÜRR DENTAL SE, Bietigheim-Bissingen (DE)

( * ) Notice: Subject to any disclaimer, the term of this patent is extended or adjusted under 35 U.S.C. 154(b) by 0 days.

(21) Appl. No.: 16/439,392

(22) Filed: Jun. 12, 2019

(65) Prior Publication Data
US 2019/0384155 A1 Dec. 19, 2019

(30) Foreign Application Priority Data

Jun. 15, 2018 (DE) .................... 10 2018 114 460

(51) Int. Cl.
*G03B 42/04* (2006.01)
*A61B 6/00* (2006.01)

(52) U.S. Cl.
CPC .......... *G03B 42/047* (2013.01); *A61B 6/4216* (2013.01); *G03B 42/042* (2013.01)

(58) Field of Classification Search
CPC .................................................. G03B 42/047
See application file for complete search history.

(56) References Cited

U.S. PATENT DOCUMENTS

| | | | |
|---|---|---|---|
| 5,202,911 A | 4/1993 | Fabian | |
| 7,140,769 B2 | 11/2006 | Kay | |
| 10,159,452 B2 | 12/2018 | Bernhardt | |
| 2005/0169433 A1* | 8/2005 | Kay | ......................... A61B 6/14 378/168 |
| 2007/0081631 A1* | 4/2007 | Kay | ..................... G03B 42/047 378/168 |

(Continued)

FOREIGN PATENT DOCUMENTS

| | | |
|---|---|---|
| DE | 102014014056 | 6/2015 |
| DE | 102016206559 | 6/2017 |

OTHER PUBLICATIONS

DE Office Action 11202018, Office Action cited in corresponding German Application No. 10 2018 114 460.1; dated Nov. 20, 2018; 6pp.

*Primary Examiner* — Hoon K Song
(74) *Attorney, Agent, or Firm* — Lempia Summerfield Katz LLC

(57) ABSTRACT

An x-ray phosphor plate system has an x-ray phosphor plate, which is configured to be exposed by x-ray light in a recording region, and which carries a shadowing marker, which is arranged in the recording region, on at least one side of the x-ray phosphor plate. The system also has a phosphor plate reader, which is configured to read the exposed x-ray phosphor plate in order to produce an x-ray recording. The shadowing marker has a shadowing effect in respect of x-ray light that is so small that the shadowing marker is only weakly identifiable, and/or only identifiable by way of image artefacts, and/or not identifiable when the x-ray recording is observed by a user. The phosphor plate reader instead has an identification algorithm, which is configured to identify whether or not the x-ray light was shadowed by the shadowing marker during the exposure.

12 Claims, 2 Drawing Sheets

(56) References Cited

U.S. PATENT DOCUMENTS

| | | | |
|---|---|---|---|
| 2010/0091951 A1* | 4/2010 | Ngo | G03B 42/047 378/163 |
| 2015/0343237 A1* | 12/2015 | Hausotte | A61N 5/1049 600/411 |
| 2017/0296131 A1 | 10/2017 | Bernhardt | |

* cited by examiner

X-RAY PHOSPHOR PLATE SYSTEM

CROSS-REFERENCE TO RELATED APPLICATION

This application claims the benefit of priority to German Patent Application No. 10 2018 114 460.1, filed in the German Intellectual Property Office on Jun. 15, 2018, the entire contents of which are incorporated herein by reference.

BACKGROUND

1. Technical Field

The invention relates to an x-ray phosphor plate system, comprising
a. an x-ray phosphor plate which is configured to be exposed by x-ray light in a recording region and which carries a shadowing marker, which is arranged in the recording region, on at least one side,
b. a phosphor plate reader which is configured to read the exposed x-ray phosphor plate in order to produce an x-ray recording.

2. Prior Art

X-ray phosphor plate systems are used in industry, medicine and/or dentistry to produce x-ray recordings of a certain examination region, such as the teeth in a jaw, for example, for a user in a timely fashion. To this end, x-ray phosphor plates are arranged downstream of the examination region to be examined by x-rays, e.g., the jaw, in relation is to an x-ray source and are exposed by x-ray light from the x-ray source. The phosphor plate then carries a latent image, which is read by the phosphor plate reader and which is displayed on a display device as an x-ray recording, in a manner comparable to conventional x-ray film recordings.

To this end, currently conventional x-ray phosphor plate systems use so-called photoluminescent phosphor plates as phosphor plates, which are scanned and read point-by-point or line-by-line in the phosphor plate reader by activation light. Therefore, such phosphor plate readers are also referred to as scanners in abbreviated form. In dentistry, in particular, use is made here of pass-through scanners, in which x-ray phosphor plates are transported through the device in one direction without a sleeve, scanned in the process and subsequently erased.

In principle, such phosphor plates can be exposed by x-ray light from one or the other side of the phosphor plate since the x-ray light completely passes through the phosphor plate. Nevertheless, many phosphor plates have distinguishable front and back sides since a one-sided readout of the phosphor plates is often preferred. In particular, the phosphor plates often have a protective coating on the back side which, for example for reasons of transportation, is fitted to certain friction wheels or belt drives in the phosphor plate reader. However, in view of the x-ray light, these coatings only have minimal attenuation effects.

Consequently, the phosphor plates have a preferred front side and a back side.

As described in U.S. Pat. No. 7,140,769 B2, what may occur during clinical daily routine is is that dental phosphor plates that are not transported in a cartridge, in particular, are inadvertently arranged with their back side facing the x-ray source instead of their front side within the scope of the exposure. This leads to mirroring in the image information of the x-ray recording.

It is therefore desirable for the side from which the phosphor plate was exposed to be identifiable during a subsequent evaluation of the x-ray recording.

As likewise described in U.S. Pat. No. 7,140,769 B2, the use of shadowing markers, which are applied on one side of the phosphor plate in a recording region of the phosphor plate, is known. These shadowing markers consist of a material with a high effective cross section for x-ray light and strongly shadow the x-ray light when the exposure is implemented from the side of the shadowing marker. As a result, the shadowing marker is visible in one case and not visible in the other case when observing the x-ray recording.

Moreover, asymmetric designs of the shadowing markers are also known in order to identify further conclusions in relation to the orientation of the phosphor plate with respect to the x-ray source or possibly occurring image transformations within the reader.

However, a disadvantage of these previous shadowing markers is that a portion of the examination region in the x-ray recording is covered, and hence becomes inaccessible to a diagnosis, when exposing the phosphor plate from the side of the shadowing marker.

SUMMARY

It is therefore an object of the invention to specify an x-ray phosphor plate system of the type set forth at the outset, which is improved in view of the shadowing marker, in particular which allows the exposure direction to be identified without image information being lost.

According to the invention, this is achieved by an x-ray phosphor plate system of the type set forth at the outset, in which
c) the shadowing marker has a shadowing effect in respect of x-ray light that is so small, in particular no more than approximately 30% of the incident x-ray intensity, that the shadowing marker is only weakly identifiable, only identifiable by way of image artefacts and/or not identifiable when the x-ray recording is observed by the user, and in which
d) the phosphor plate reader has an identification algorithm which is configured to identify whether or not the x-ray light was shadowed by the shadowing marker during the exposure.

In contrast to the known systems, the inventors have recognized that it is not necessary to provide a shadowing marker with a pronounced shadowing effect, which causes the shadowing marker to be directly visible to the user in the ultimately displayed x-ray recording in the case of a normal observation. Instead, the inventors propose the provision of a shadowing marker with such a low shadowing effect that the shadowing marker is not visible, or at best only weakly visible, in the actual x-ray recording usually presented to the user.

In particular, diagnoses should still be able to be made using the x-ray recording as a result of the low shadowing effect. That is to say, the structures of interest for the respective diagnosis should remain identifiable. This is particularly advantageous if structures to be examined are situated in the part of the recording region in which the shadowing marker is also arranged.

Here, image artefacts are also understood to mean that only some of the shadowing marker is visible since other parts are overlaid by structures to be examined.

Consequently, the x-ray recording is only slightly restricted in terms of its dynamic range by such a shadowing marker at the shadowed points.

In order nevertheless to determine the side from which the phosphor plate was exposed, an identification algorithm is provided in the reader, said identification algorithm specifically being configured to identify the only small shadowing caused by the is shadowing marker and accordingly determine the exposure side.

To this end, the identification algorithm can seek for, e.g., a possibly present image artefact such as a weak shadow, for example.

However, such image artefacts do not prevent the identifiability of the actual structures of the examination region since the shadowing effect is so small.

Since the shadowing effect generally depends on the employed marker material and exposure parameters such as, for example, x-ray voltage, x-ray intensity, signal-to-noise ratio of the x-ray recording, etc., very different precise configurations of the shadowing marker are possible, which each depend on the expected exposure parameters and the expected examination regions. However, the deliberations according to the invention allow a suitable selection to be made for any application case in order to achieve, firstly, only weak visibility in the case of normal observation and, secondly, a sufficient robustness of the identification algorithm.

Within the scope of the invention and in conjunction with the identification algorithm, the phosphor plate reader is naturally understood to mean both a phosphor plate reader in which the identification algorithm is directly integrated in a separate scanner unit for the readout and a phosphor plate reader which comprises corresponding evaluation software with the identification algorithm in a separate data processing device such as a commercially available PC. Additionally, it is unimportant here as to whether the identification algorithm is implemented in hardware or in software or even as an outsourced service on a server.

Here, an x-ray recording is understood to mean any representation of the x-ray intensity distribution. The measured intensity values are usually stored in a two-dimensional array or already saved as greyscale values.

In one embodiment, provision is made for the shadowing marker to have a geometric form with a characteristic feature and for the identification algorithm to use the characteristic feature to identify a possible shadowing effect.

As a result, the identification algorithm can seek for the shadowing effect in the evaluated image in a targeted fashion and can ascertain whether or not a shadowing effect, i.e., an appropriate exposure on the part of the shadowing marker, has taken place. Consequently, a reliable identification can occur provided that the characteristic feature is not also present in the examination region to be examined by x-rays. By way of example, a characteristic feature can be a dimension of the shadowing marker.

In one embodiment, provision is made for the shadowing marker to have a defined periodicity and the identification algorithm to evaluate the x-ray recording in view of the periodicity.

Periodic structures typically do not occur in the examination region if the x-ray phosphor plate system is used in medicine and dentistry. Therefore, a shadowing marker with a periodicity known in advance, for example in terms of its geometric form and/or its shadowing effect, can be reliably identified by the identification algorithm.

In one embodiment, provision is made for the identification algorithm to convert the x-ray recording from real space to a frequency space and to seek for a frequency belonging to the periodicity of the shadowing marker in the frequency space.

A periodicity can be identified particularly well in the frequency space. Here, an option is represented by the conversion into Fourier space, for example by way of the discrete Fourier transform (DFT).

However, on account of the relationship between real space and frequency space and corresponding image evaluation filters, such a periodicity of the shadowing marker may also occur with other image filters, which optionally operate directly in real space.

In one embodiment, provision is made for the shadowing marker to be at least a part of a radio marker attached to the phosphor plate.

Radio markers, in particular RFID markers, are frequently used in engineering to individualize a multiplicity of objects by virtue of a unique ID, which can be read by radio, is being assigned to the objects. This may also be advantageous in the case of phosphor plates since the respective phosphor plate is then directly or, with the aid of an appropriate database, indirectly assignable to certain exposure processes and/or patients. Additionally, the radio markers can determine readout parameters that lead to an optimal readout in the phosphor plate reader. To this end, corresponding radio read and/or write devices may be provided at the x-ray exposure apparatus and at the phosphor plate reader.

Therefore, for production reasons, it is advantageous to use a radio marker, provided on one side of the x-ray phosphor plate in any case, as a shadowing marker at the same time.

In one embodiment, provision is made here for the identification algorithm, when identifying the shadowing, to access information items respectively linked to the individual radio marker.

By way of example, a database may contain a characteristic feature of the respective radio marker such that, after reading the radio marker information, the identification algorithm can seek the relevant shadowing features in a targeted manner.

Thus, for example, the shadowing identification on different phosphor plate sizes is improved or a change of the employed radio markers to differently designed radio markers is facilitated within the scope of product care by virtue of the identification algorithm obtaining the appropriate information.

In one embodiment, provision is made for the shadowing marker to be an antenna structure of the radio marker.

By way of example, such an antenna structure can be the antenna of an RFID marker.

In one embodiment, provision is made for the antenna structure of the radio marker to have a spiral form and the identification algorithm to seek for a characteristic feature of the spiral form in the x-ray recording and to determine whether or not a is shadowing effect is present therefrom.

A spiral antenna structure has approximately the same distances between the spiral arms, said distances repeating multiple times such that a periodicity is present. In turn, this periodicity can be identified very well in the frequency space.

In one embodiment, provision is made for the shadowing marker to be made of an electrically conductive material.

This allows the shadowing marker to be used for other purposes, such as an antenna structure, for example, at the same time.

To this end, the shadowing marker can be made of copper, for example.

However, it can also be made of a light metal, in particular aluminium. A shadowing marker made of light metal only causes little shadowing of the x-ray light since the x-ray interaction cross section thereof is small.

In one embodiment, provision is made for the shadowing marker to be printed onto the x-ray phosphor plate as printing ink with the aid of a printing method.

A printing method, such as screen printing, for example, represents a simple manufacturing process for the shadowing marker on an x-ray phosphor plate. By way of example, the printing ink may comprise barium sulphate for the shadowing effect.

In one embodiment, provision is made for the shadowing marker to cause a shadowing effect of less than approximately 20% of the incident x-ray intensity. In one embodiment, the shadowing marker causes a shadowing effect of less than approximately 10% of the incident x-ray intensity. In one embodiment, the shadowing marker causes a shadowing effect of less than approximately 5% of the incident x-ray intensity.

Such a low shadowing effect ensures that the shadowing marker is just not visible in the case of an observation in which the structures of interest of the examination region to be examined by x-rays are just still identifiable by the user.

In one embodiment, provision is made for the shadowing marker to cause a is shadowing effect of more than approximately 1% of the incident x-ray intensity. In one embodiment, the shadowing marker causes a shadowing effect of more than approximately 2% of the incident x-ray intensity. In one embodiment, the shadowing marker causes a shadowing effect of more than approximately 4% of the incident x-ray intensity.

A lower limit for the shadowing effect guarantees a sufficient robustness of the identification algorithm in order to determine without doubt whether or not an incorrect exposure is present.

BRIEF DESCRIPTION OF THE DRAWINGS

Embodiments of the invention are explained in more detail below on the basis of the drawings. In these.

DETAILED DESCRIPTION

Figure 1:
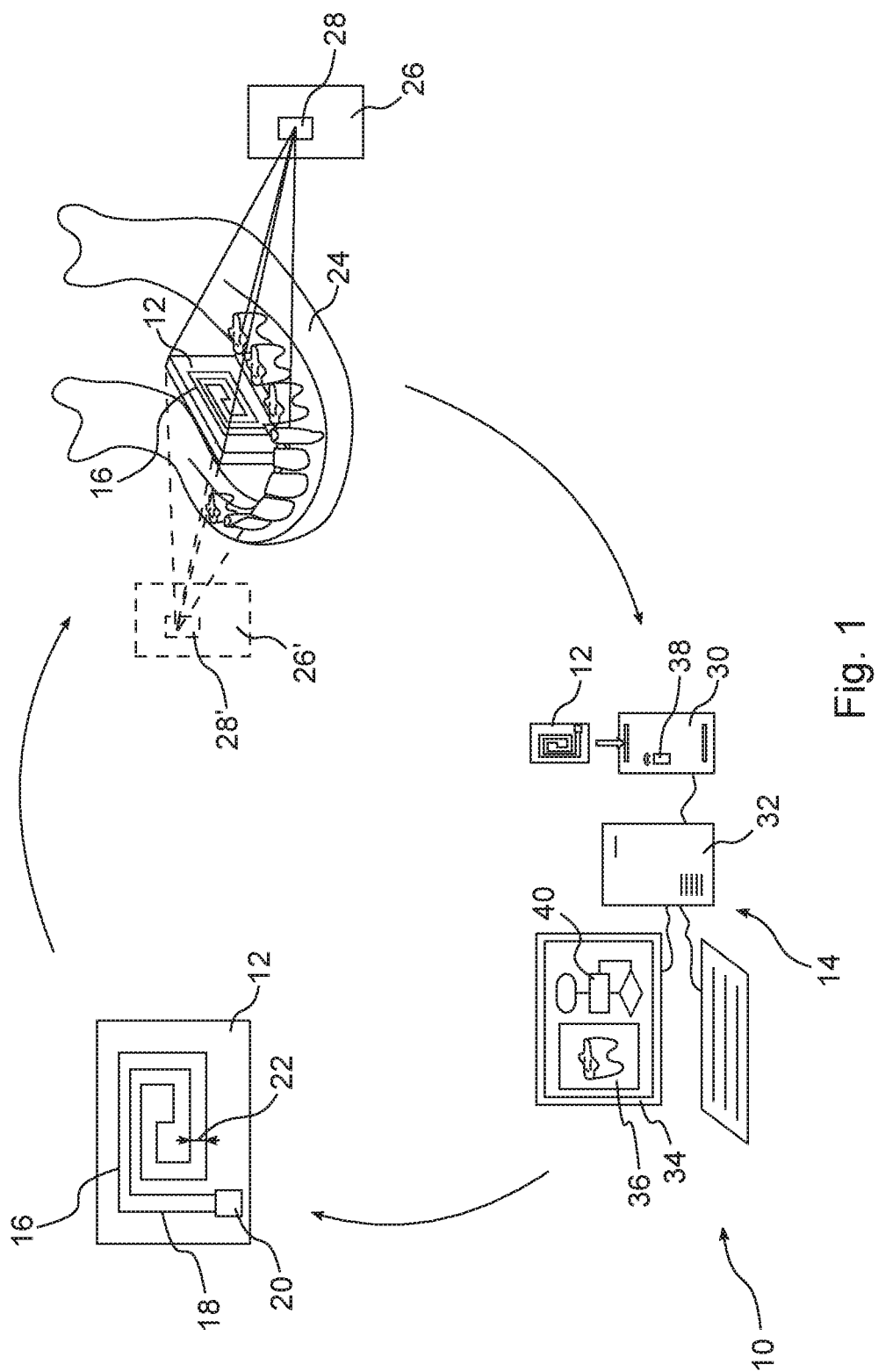
FIG. 1 shows a schematic illustration of an x-ray phosphor plate system with a shadowing marker.

FIG. 1 shows overall the typical cycle of an x-ray recording in dentistry with an x-ray phosphor plate reader system 10 illustrated in the lower part of FIG. 1.

The x-ray phosphor plate readout system 10 comprises an x-ray phosphor plate 12 and a phosphor plate reader 14.

As visible from FIG. 1, top left, the x-ray phosphor plate 12 has a shadowing marker 16, which is arranged on one side of the x-ray phosphor plate 12, typically the back side thereof. The shadowing marker 16 is at least also arranged in a recording region of the x-ray phosphor plate 12 that is provided for the actual exposure. In relation to previously known shadowing markers 16 made of copper, for example, the shadowing marker 16 however only has a small shadowing effect.

In the exemplary embodiment shown here, the shadowing marker 16 is embodied as a spiral antenna structure 18 of an RFID marker 20, which individualizes the x-ray phosphor plate 12 for the purposes of a simpler assignment in relation to other x-ray phosphor plates 12 of the x-ray phosphor plate readout system 10.

The spiral form of the antenna structure 18 has a distance 22 between the individual aluminium conductor tracks that is predetermined by the electromagnetic properties and that remains substantially unchanged along the spiral form.

With the unchanging distance 22, the shadowing marker 16 in the exemplary embodiment shown here has periodically alternating regions of aluminium conductor tracks and interstices between the conductor tracks as a characteristic feature.

As shown in the right, upper part of FIG. 1, the x-ray phosphor plate 12 is introduced into the interior of a jaw 24 for exposure purposes and exposed by an x-ray exposure apparatus 26, which is not necessarily a part of the x-ray phosphor plate system 10, and an x-ray source 28 arranged therein.

Here, the back side of the x-ray phosphor plate 12 that carries the shadowing marker 16 faces the x-ray source 28, and so the exposure is implemented on the side of the shadowing marker 16. This corresponds to an inadvertently incorrectly inserted x-ray phosphor plate 12.

For an improved understanding of the different exposure directions, a complementary position of the x-ray exposure apparatus 26' and the x-ray source 28' is furthermore shown using dashed lines.

After the exposure of the x-ray phosphor plate 12, the latter is introduced into the phosphor plate reader 14. For reading the phosphor plate 12, the phosphor plate reader comprises, in a scanner unit 30, the components that are known from such phosphor plate readers 14.

Here, the scanner unit 30 is embodied as a pass-through scanner; however, use can be made of any scanning method that is suitable for capturing the photoluminescence of x-ray phosphor plates 12.

Further, the scanner unit 30 comprises an RFID reader 38, by means of which the information of the RFID marker 20 is read by radio.

The read data of the x-ray recording and, optionally, the information from the RFID marker 20 are subsequently transmitted to an evaluation unit 32, which is represented here as a commercially available PC.

A conventional greyscale value image 36 of the x-ray recording can be displayed on a display device 34 of the evaluation unit 32. However, on account of its low shadowing effect, the shadowing marker 16 is not identifiable by the user in this greyscale value image 36 in the case of a normal observation.

Therefore, the evaluation unit 32 has an identification algorithm 40, which is configured to identify the side from which the x-ray phosphor plate 12 was exposed by virtue of seeking for a shadowing effect of the shadowing marker 16 in the x-ray recording.

Figure 2:
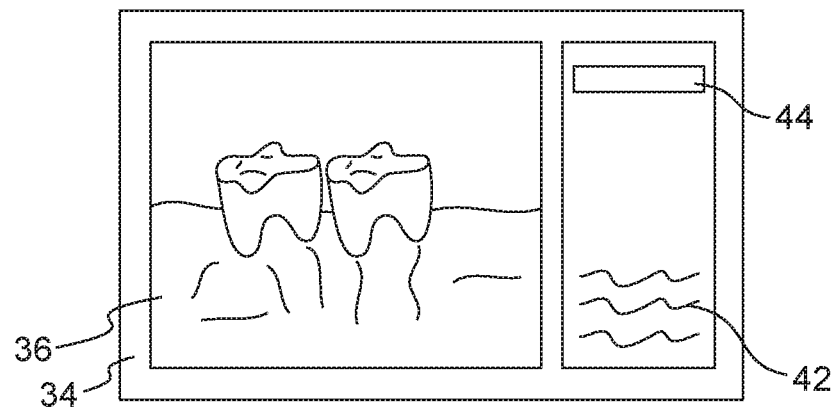
FIG. 2 shows a representation of an x-ray recording shown to the user in the case of a normal observation, with the exposure having been implemented on the side of the shadowing marker.

The identification algorithm 40 operates as follows:

The identification algorithm 40 receives as input information the x-ray recording, which was presented to the user as a greyscale value image 36, which is shown again in FIG. 2. As is clear from FIG. 2, patient information 42 is displayed next to and/or over the greyscale value image 36.

Furthermore, an incorrect exposure notification 44 is provided, which indicates the side from which the x-ray phosphor plate 12 was is exposed.

As is once again clear from FIG. 2 as well, no optical conclusions about the presence of the shadowing effect by the shadowing marker 16 can be drawn by the user from this greyscale value image 36, which is provided for a normal observation by an operator.

The identification algorithm 40 now converts the x-ray recording from real space into the frequency space by virtue of the image data being subjected to a Fourier transform. A representation of the corresponding frequency space image 46 could approximately look like what is shown in FIG. 3.

Figure 3:
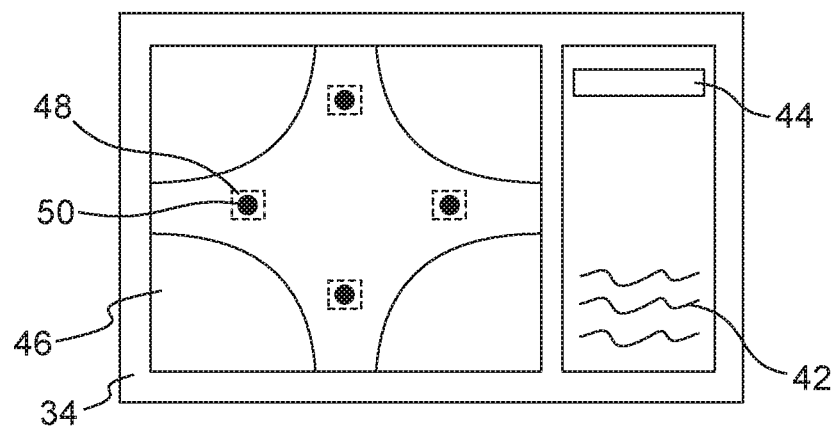
FIG. 3 shows a frequency space image of this x-ray recording after a transformation of the x-ray recording into the frequency space.

On account of the periodicity of the antenna structure 18 with the distance 22, intensity peaks 50 are formed at positions 48 in the frequency space image 46 that are defined by the periodicity, as is clear from FIG. 3.

Therefore, the identification algorithm 40 seeks for the presence of such intensity peaks 50 at the positions 48 which are known in advance.

Here, the positions 48 which are known in advance can be determined depending on the information obtained by the RFID marker 20 in relation to the x-ray phosphor plate 12 and hence also in relation to the shadowing marker 16 applied thereto.

Consequently, by applying decision criteria, the identification algorithm 40 determines on account of intensity peaks 50 being present in the present example that an exposure of the x-ray phosphor plate from the side of the shadowing marker 16 is present.

Figure 4:
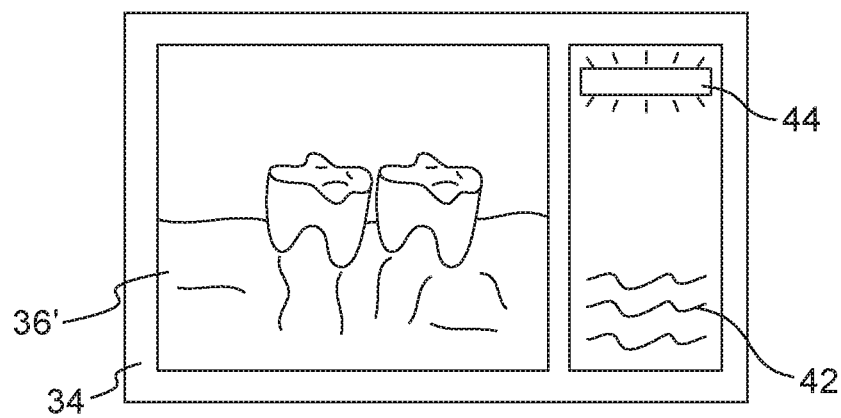
FIG. 4 shows a representation of the x-ray recording of FIG. 2, which was mirrored on account of the exposure on the side of the shadowing marker and which shows an informative indication in respect of the exposure side.

Therefore, as shown in FIG. 4, the identification algorithm 40 can activate the incorrect exposure notification 44, from which it becomes clear that an exposure was carried out from the side of the shadowing marker 16.

Further, the x-ray recording can now be mirrored on account of the identification of the shadowing effect such that the greyscale value image 36' shown in FIG. 4 shows the correct orientation of the jaw 24.

Additionally, the identification algorithm 40 may also have a shadowing marker suppression algorithm, which negates the effects caused by the shadowing effect, such as a slight background shadow, for example.

Naturally, the identification algorithm 40 may dispense with the presentation of the intermediate steps, and so only the final greyscale value image 36' is displayed to the user.

The invention claimed is:

1. An X-ray phosphor plate system comprising:
an x-ray phosphor plate, which is configured to be exposed by x-ray light in a recording region, and which carries a shadowing marker, which is arranged in the recording region, on at least one side of the x-ray phosphor plate; and
a phosphor plate reader, which is configured to read the exposed x-ray phosphor plate in order to produce an x-ray recording, wherein
the shadowing marker has a shadowing effect in respect of x-ray light that is no more than approximately 30% of the incident x-ray intensity such that the shadowing marker is only weakly identifiable, and/or only identifiable by way of image artefacts, and/or not identifiable when the x-ray recording is observed by a user, and
wherein the phosphor plate reader has an identification algorithm, which is configured to identify whether or not the x-ray light was shadowed by the shadowing marker during the exposure.

2. An X-ray phosphor plate system according to claim 1, wherein the shadowing marker has a geometric form with a characteristic feature, and wherein the identification algorithm uses the characteristic feature to identify a possible shadowing effect.

3. An X-ray phosphor plate system according to claim 1, wherein the shadowing marker has a defined periodicity and the identification algorithm evaluates the x-ray recording in view of the periodicity.

4. An X-ray phosphor plate system according to claim 3, wherein the identification algorithm converts the x-ray recording from real space to a frequency space and seeks for a frequency belonging to the periodicity of the shadowing marker in the frequency space.

5. An X-ray phosphor plate system according to claim 1, wherein the shadowing marker is at least a part of a radio marker attached to the x-ray phosphor plate.

6. An X-ray phosphor plate system according to claim 5, wherein the shadowing marker is an antenna structure of the radio marker.

7. An X-ray phosphor plate system according to claim 6, wherein the antenna structure of the radio marker has a spiral form and the identification algorithm seeks for a characteristic feature of the spiral form in the x-ray recording and determines whether or not a shadowing effect is present therefrom.

8. An X-ray phosphor plate system according to claim 1, wherein the shadowing marker is made of an electrically conductive material.

9. An X-ray phosphor plate system according to claim 1, wherein the shadowing marker is printed onto the x-ray phosphor plate as printing ink with the aid of a printing method.

10. An X-ray phosphor plate system according to claim 1, wherein the shadowing marker causes a shadowing effect of less than approximately 20% of the incident x-ray intensity.

11. An X-ray phosphor plate system according to claim 1, wherein the shadowing marker causes a shadowing effect of less than approximately 10% of the incident x-ray intensity.

12. An X-ray phosphor plate system according to claim 1, wherein the shadowing marker causes a shadowing effect of less than approximately 5% of the incident x-ray intensity.

* * * * *